United States Patent [19]

Sukkarie

[11] 4,202,328
[45] May 13, 1980

[54] METHOD AND MEANS FOR FIXATION AND IMMOBILIZATION OF THE JAWS

[76] Inventor: Ghassan A. Sukkarie, 32037 Concord Dr., Madison Heights, Mich. 48071

[21] Appl. No.: 854,272

[22] Filed: Nov. 23, 1977

[51] Int. Cl.² .............................................. A61F 5/04
[52] U.S. Cl. ..................... 128/89 A; 433/4; 433/18
[58] Field of Search ........................... 32/14 A, 40 R; 128/89 A

[56] References Cited

U.S. PATENT DOCUMENTS

| | | | |
|---|---|---|---|
| 473,040 | 4/1892 | Wilder | 32/14 A |
| 1,638,006 | 8/1927 | Aderer | 32/14 A |
| 1,797,481 | 3/1931 | Preston | 32/14 A |
| 2,502,902 | 4/1950 | Tofflemire | 32/14 A |
| 3,487,545 | 1/1970 | Weissman | 32/14 A |
| 3,879,850 | 4/1975 | Wallshein | 32/14 A |
| 3,936,938 | 2/1976 | Northcut | 32/14 A |

FOREIGN PATENT DOCUMENTS 601835  2/1933  Fed. Rep. of Germany .......... 32/14 A

*Primary Examiner*—Louis G. Mancene
*Assistant Examiner*—John J. Wilson

*Attorney, Agent, or Firm*—Robert G. Mentag

[57] ABSTRACT

A method and means for the fixation and immobilization of a patient's jaws for use in the oral surgery art. An arch bar is disposed around the exterior of a patient's teeth, either the lower or upper teeth, in accordance with the particular oral surgery problem to be solved. The arch bar is a flat strip of soft stainless steel which is secured to the teeth by a plurality of arch wires. Each of the arch wires is disposed between two adjacent teeth, and it has a knob on the inner end for fitting against the lingual-gingival embrasure of two adjacent teeth. Each arch wire has a number of spaced apart beads of varying diameter which are adapted to pass through an opening in the arch bar in only one direction so as to secure the arch bar to the outer side of the teeth. A special cutting pliers is provided for cutting off the excess length of an arch wire after it is secured to an arch bar. An arch bar and securing wires can be used on each of the upper and lower teeth. The upper and lower arch bars in such instance are each provided with a plurality of hooks which are connected by a suitable retaining means, as an elastic retaining member or a wire type retaining member, for fixing the upper and lower jaws together.

10 Claims, 17 Drawing Figures

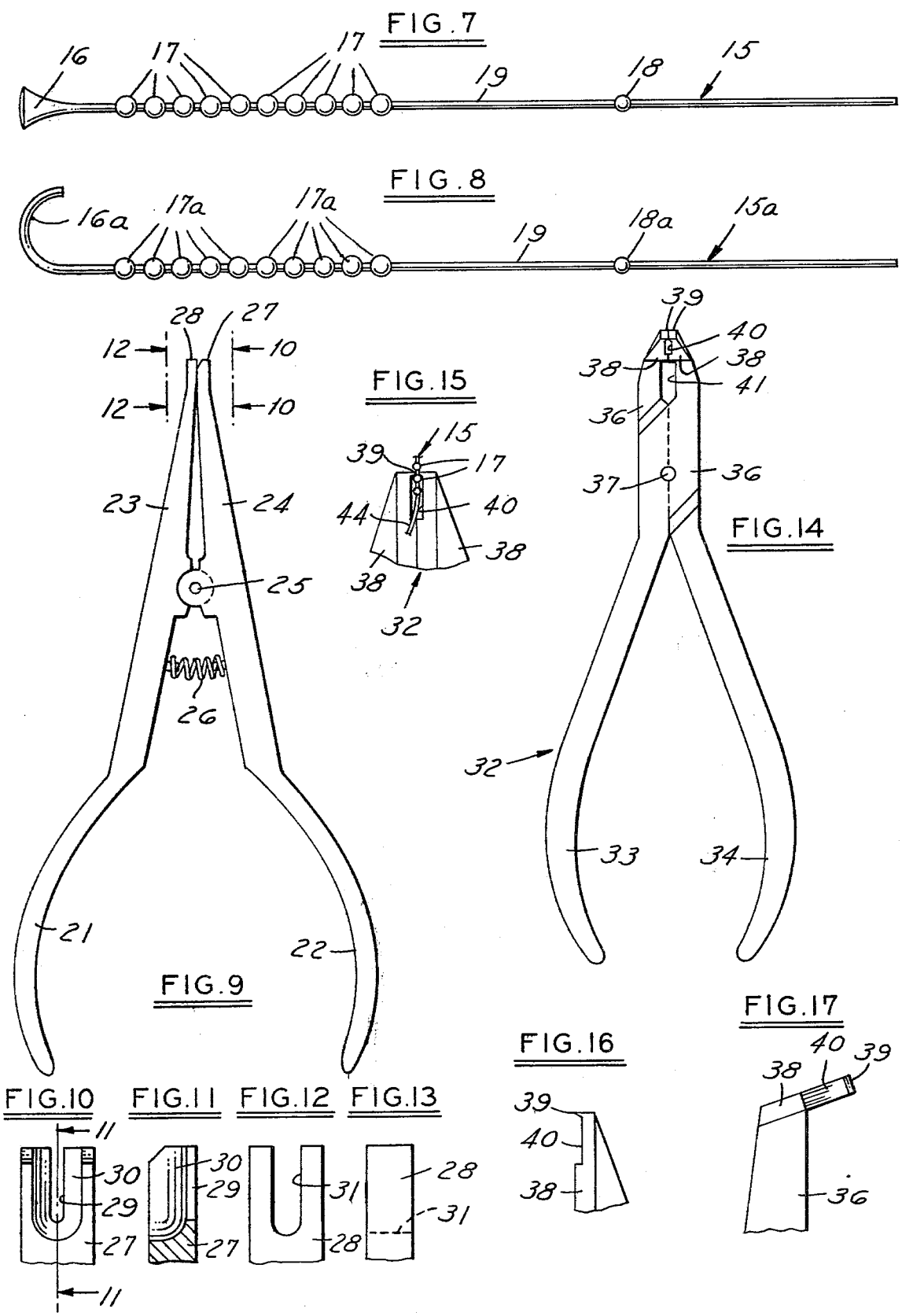

METHOD AND MEANS FOR FIXATION AND IMMOBILIZATION OF THE JAWS

BACKGROUND OF THE INVENTION

1. Field of the Invention

This invention relates to the oral surgery art, and more particularly to a novel and improved method and means for the fixation and immobilization of a patient's jaws, due to various reasons wherein the jaw fixation is required for surgical purposes. The invention is specifically adapted to instances where a patient has a sufficient number of teeth in different segments of the jaws for use as an anchor or support means.

2. Description of the prior art

It is well known in the oral surgery art to employ impressions or casts for oral surgery purposes, as in cases where cast type splints or split acrylic splints are used. Other methods have also been employed in the correction of jaw deformities and the like. For example, implants in the jaw bones of a patient have been used for the fixation and immobilization of a patient's jaws. Also, conventional type arch bars and arch wires have been used.

A disadvantage of the aforementioned prior art methods for the fixation and immobolization of the jaws is that they are difficult and time consuming to employ. Furthermore, they must be carried out in an operating room under high cost conditions. A disadvantage of the prior art type of arch wires is that they sometimes loosen in use, and the sharp ends of the arch wires sometimes cause irritation of the soft tissues in a patient's mouth. The aforementioned prior art methods for the fixation and immobilization of jaws sometimes interfere with the occlusion or complete closure of a patient's teeth, and thus create a need for post operative selective grinding and correction of the occlusion.

SUMMARY OF THE INVENTION

In accordance with the present invention, the arch bar is cut to the dimensions of the distance between the distal of the last right tooth and the distal of the last left tooth of the same jaw. The arch wire is passed by a hemostat from the inner side, or the lingual side of the tooth, between two adjacent teeth and below the contact areas of the two adjacent teeth and out to the buccal side of the tooth. The arch wire is passed through a hole in the arch bar which permits only the first bead of a plurality of beads on the arch wire to pass freely therethrough, due to its outer diameter being smaller than the diameter of the hole in the arch bar.

A tying plier is then used for securing the arch wire to the arch bar. The tying plier has a pair of specially designed beaks which include a lower beak that is positioned against the arch bar, and an upper beak which engages the first bead on the arch wire. The tying plier beaks are then spread apart, and the arch bar through which the arch wire is passed permits the beads on the arch wire which are positioned after the first bead to go through the hole in the arch bar in one direction only. The application of a plurality of arch wires in the last described manner secures the arch bar on the teeth of the jaw in a number of desired positions. An arch wire can be disposed between each two adjacent teeth, or arch wires can be placed around the jaw in any desired fashion. The extra length of the arch wire is cut off by a specially designed cutting plier which holds the cut-off free end of the arch wire so that it will not drop off into the mouth of a patient, or injure the soft tissue of the patient's mouth. After the extra length of arch wire is cut off, there is only one bead which is in direct contact with the arch bar for securing the arch wire to the arch bar. The bead on the outer end of each arch wire is round and does not have any sharp ends. The cut free end of each arch wire is held in the jaws of the cutting plier and can be removed or taken out of the operating field in the mouth of a patient in a safe manner. An arch bar may be mounted on each of the jaws in the last described manner, and in such case, the arch bars are provided with hooks which are interconnected by a suitable retainer member, such as a wire member for fixing the jaws together. The tying pliers is provided with a particularly shaped lower beak which permits the arch wire with its beads to pass therethrough. The tying pliers is also provided with an upper beak which is adapted to engage the first bead on an arch wire to grip the arch wire for stretching it into a secure position with the arch bar. The cutting pliers is provided with angled cutting beaks which are also shaped to grasp the cut free end of an arch wire and hold it, for removing the same from the mouth of a patient in a safe and efficient manner.

Other objects, features and advantages of this invention will be apparent from the following detailed description, appended claims, and the accompanying drawings.

BRIEF DESCRIPTION OF THE DRAWINGS

FIG. 7 is a side view of an arch wire.

FIG. 8 is a side view of a modified arch wire.

FIG. 9 is an elevational view of a tying plier employed in the invention.

FIG. 10 is a side view of the upper beak on the tying plier of FIG. 9, taken along the line 10—10 thereof, and looking in the direction of the arrows.

FIG. 11 is an elevational section view of the upper beak shown in FIG. 10, taken along the line 11—11 thereof, and looking in the direction of the arrows.

FIG. 12 is a side view of the lower beak on the tying plier of FIG. 9, taken along the line 12—12 thereof, and looking in the direction of the arrows.

FIG. 13 is an elevational left side view of the lower beak on the tying plier of FIG. 9, taken along the line 13—13 thereof, and looking in the direction of the arrows.

FIG. 14 is a side view of the cutting plier employed in the invention.

FIG. 15 is a fragmentary view of the beaks of the cutting plier and showing the cutting off of an arch wire free end.

FIG. 16 is a fragmentary top plan view of one of the beaks on the cutting plier of FIG. 14.

FIG. 17 is a side elevation view of a beak on the tying plier of FIG. 14.

DESCRIPTION OF THE PREFERRED EMBODIMENTS

The method of the present invention employs an arch bar, a plurality of arch wires, a tying plier, and a cutting plier.

Figure 1:
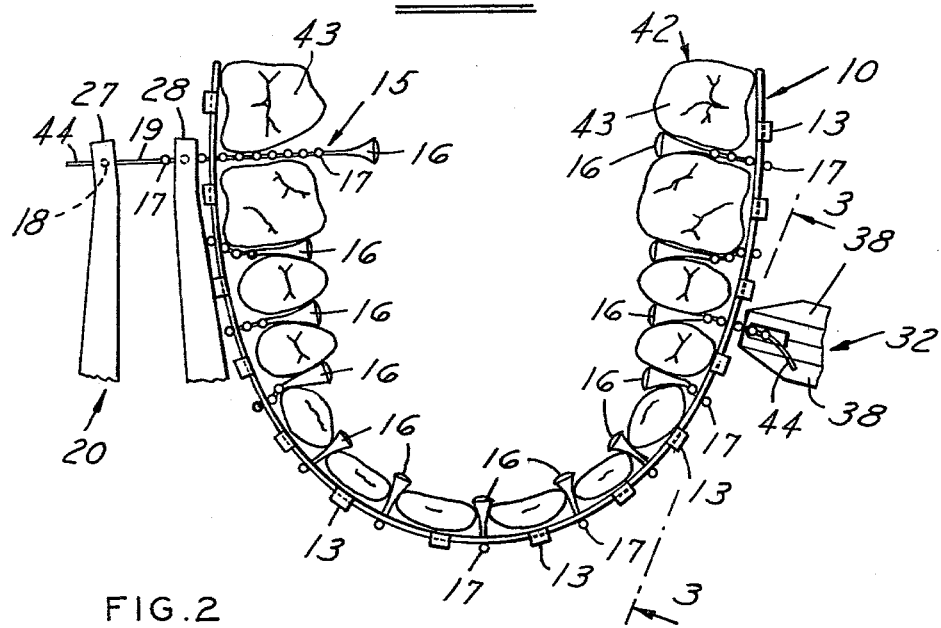
FIG. 1 is a plan view of a lower jaw provided with an arch bar in accordance with the principles of the invention.
Figure 4:
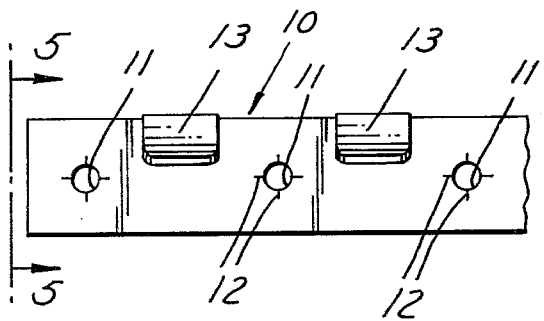
FIG. 4 is a fragmentary side elevational view of an arch bar employed in the invention.
Figure 5:
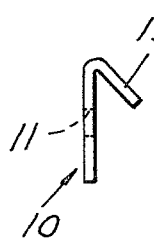
FIG. 5 is a left side view of the arch bar structure illustrated in FIG. 4, taken along the line 5—5 thereof, and looking in the direction of the arrows.

As shown in FIG. 4, the arch bar is generally indicated by the numeral 10, and it comprises a flat strap of soft stainless steel which is tied to the buccal and labial surfaces of teeth as shown in FIG. 1. The arch bar 10 is provided with a plurality of circular holes 11 which have cuts or slits 12 formed around the periphery thereof. The holes 11 allow passage of an arch wire through the arch bar 10. The arch bar 10 has three or more cuts 12 around each hole 11. Preferably, four cuts 12 are used around each hole 11.

The arch bar 10 is provided with integral hooks 13 along the outer side thereof. The hooks 13 are bent at about a 45° angle relative to the arch bar outer face. The arch bar 10 is made in rolls to avoid waste of such material.

In one embodiment, the arch bar 10 was 4 mm. high, and 0.75 mm. thick. The length of the hook 13 was 2 mm. and it was spaced about 1 mm. from the adjacent face of the arch bar.

Figure 6:
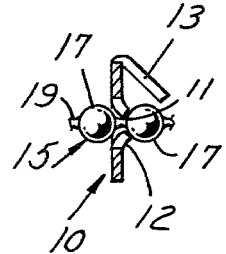
FIG. 6 is an elevational view through the arch bar structure of FIG. 3, taken along the line 6—6 thereof, and looking in the direction of the arrows.

FIG. 7 shows an arch wire indicated generally by the numeral 15. The arch wire 15 comprises a knob 16 which is preferably triangular in rear elevation. The arch wire 15 has an elongated wire body 19 that has one end integral with the knob 16. Ten beads 17 are integrally formed on the wire body 19 in preferably evenly spaced positions. The bead 17 nearest the knob 16 is spaced about 2 mm. from the adjacent end of the knob 16. The beads 17 are spaced about 0.6 mm. apart, and they are about 1.25 mm. in diameter. The arch wire body 19 is about 0.8 mm. in diameter. An eleventh integral bead 18 is spaced apart from the first bead 17 by about a distance of 6 mm. The bead 18 is smaller in diameter than the hole 11 in the arch bar 10 to allow it to pass freely therethrough. The beads 17 are slightly larger in diameter than the arch bar holes 11, but they will pass therethrough in one direction when the arch wire is stretched by the plier and be trapped in the arch bar as shown in FIG. 6. The arch wire 15 is made of stainless steel.

FIG. 8 shows as modified arch wire indicated by numeral 15a. The part of the arch wire 15a which are the same as the arch wire 15 of FIG. 7 have been marked with the same reference numerals followed by the small letter "a."

The arch wire 15a is provided with a hook shaped knob 16a instead of the triangularly shaped knob 16. The arch wire 15a would be used where the arch wire must be hooked around an isolated single tooth.

The tying plier is made of stainless steel, and it is indicated generally in FIG. 9 by the numeral 20. The tying plier 20 includes two outwardly curved arms 21 and 22 which are integral with two jaws 23 and 24, respectively. The jaws 23 and 24 are pivotally connected by a suitable pivot shaft 25, and they are normally biased together by a suitable coil spring 26. Integrally formed on the outer ends of the jaws 23 and 24 are what may be called the upper and lower beaks 27 and 28, respectively. When the arms 21 and 22 are pressed together the beaks 27 and 28 are moved apart to an open position.

The upper beak 27 is rectangular in shape, and it has a central longitudinal slot 29 (FIG. 10) formed therethrough made to a cross section size to let only the arch wire body 19 pass therethrough, and not the beads 17 and 18. The outer face of the beak 27 is provided with an inwardly curved or concave recess 30 which is bisected by the slot 29. The slot 29 extends inwardly from the outer end of the beak 27.

The lower beak 28 is also rectangular in shape, and it has a central, longitudinal slot 31 (FIG. 12) formed from the outer end thereof. The slot 31 is large enough to allow the arch wire body 19 and the beads 17 and 18 to pass therethrough, but not the knob 16.

The cutting plier is indicated generally in FIG. 14 by the numeral 32. The cutting plier 32 includes two ovoid arms 33 and 34 which each have an integral jaw 36. The jaws 36 are identical and are pivotally connected by a suitable pivot shaft 37. The jaws 36 have identical, integral beaks 38. When the handles 33 and 34 are pressed together, the beaks are moved together.

The beaks 38 are disposed at an angle of about 135° relative to the longitudinal axis of the jaws 36. The jaws 36 and beaks 38 are made of Tungsten carbide, and the rest of the cutting pliers 32 is made of stainless steel.

A cutting edge 39 is formed on the outer end of each beak 38. The cutting edges meet along a straight line as shown in FIG. 14. A recess 40 is formed along the inner face of each beak 38 inside of each cutting edge 39 to form a space between the beaks 38 when they are closed in a cutting position. As shown in FIG. 14, the upper ends of the jaws are spaced apart when the beaks 38 are closed, as indicated by the numeral 41.

The method of the invention is illustrated in FIG. 1. The numeral 42 generally indicates a set of lower teeth around which is mounted an arch bar 10. FIG. 1 shows the arch bar 10 secured to the teeth 43 by a plurality of arch wires 15.

The arch bar 10 is cut to the dimension of the distance between the distal of the last right tooth 43 and the distal of the last left tooth 43. Each of the arch wires 15 is passed from the lingual side of the teeth 43, below the contact area of two adjacent teeth and to the buccal side of the teeth, and thence through one of the holes 11 in the arch bar 10.

As shown in FIG. 1, the tying plier 20 is then applied to the outer end of the arch wire 15. The upper beak 27 engages the bead 18 and the lower beak 28 rests against the arch bar 10. The arch wire is tightened by pressing the handles 21 and 22 together. The slot 31 in beak 28 permits the beads 17 to pass through. The holes 11 in the arch bar 10 also allow the beads 17 to pass to the buccal or other side. When the arch wire 15 is tight, the last bead 17 to pass through the hole 11 will move back against the edges of the material around the hole 11 to hold the arch wire tight when the tying plier 20 is released. The free end 44 of the arch wire 15 is then cut off, as illustrated in FIG. 1 by the cutting plier 32. The cut free end 44 is held by the plier beaks 38 in the space formed by the recesses 40 because the diameter of the arch wire body 19 is approximately the size of the width of the space formed by the recesses 40 so as to provide a friction grip on the free cut end 44.

Figure 2:
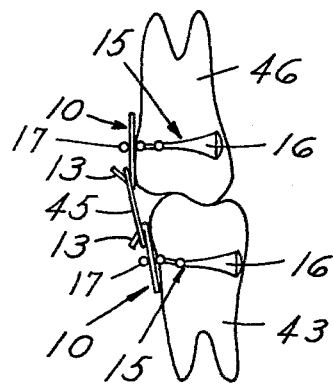
FIG. 2 is a fragmentary elevational view of a pair of jaws fixed together by the method of the present invention.
Figure 3:
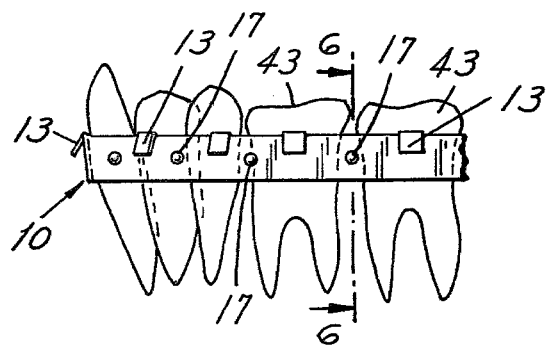
FIG. 3 is a fragmentary, left side elevational view of the teeth and arch bar structure illustrated in FIG. 1, taken along the line 3—3 thereof, and looking in the direction of the arrows.

FIG. 2 illustrates how arch bars may be applied to both jaws of a patient. A loop shaped retainer member 45 is operatively mounted around adjacent hooks 13 on the opposed arch bars 10 to fix the two jaws together. It will be understood that the upper arch bar 10 on the upper teeth 46 is mounted so as to have the hooks 13 extend upwardly while the lower arch bar 10 on the teeth 43 is mounted to have the hooks 13 extend downwardly in positions opposite to the positions of the hooks 13 on the upper arch bar 10.

There is no need to bend or cover the end of the arch wire at the point where the free end is cut off because the outer bead 17 is round and it does not have a sharp end, as shown in FIG. 6. The free end of the arch wire is cut off at the round surface of the bead 17 so as to leave a round surface. The hooks 13 of the arch bar 10 are also made so that they will have a protective function to prevent contact of the bead 17 and any resultant friction with the buccal or labial mucosa because the hooks 13 extend outwardly beyond the outer beads 17.

The method of the present invention for the fixation and immobilization of jaws can be used for oral surgery purposes whenever jaw fixation is required, and there are a number of teeth in different segments of the jaws for securing arch bars thereto. This method cannot be used where a patient has too few teeth, or dentures.

It has been found that the method of this invention provides an efficient method for jaw fixation in orthognathic surgery where you have single or multiple osteotomies. This method is advantageous where it is necessary to cut through the bone of a patient's jaw for surgical corrections, like malfunctions or disease. This method of jaw fixation may also be employed in cases where surgery of the jaw joint is required, as in the case of arthritis. This method of jaw fixation may also be used for oral surgery involving cancer of the jaw, diseases of the jaw, jaw fractures and other instances where it is necessary to fix the jaws together in order to prevent their fracture.

The advantages of the method of jaw fixation of the present invention are numerous. This method is very simple, and does not require extra skill or technique for use of the same. It is efficient, time-wise since it takes less time to insert the arch bar of the present invention than the time necessary for inserting a conventional arch bar. The arch bar 10 can be applied in a clinic prior to the day of surgery, so that operating time and costs are lower than when employing the prior art methods of jaw fixation. The arch wire 15 of the present invention does not loosen, as is the case with conventional wires employed for jaw fixation. Furthermore, the free cut-off part of the arch wire 15 is retained in the cutting plier so that there is no danger of dropping it into the mouth or throat of a conscious or unconscious patient. Also there is no need for any extra hand to hold the free end of the arch wire 15 prior to cutting it off. The present method of jaw fixation also does not need impressions or casts, as is required in the prior art cast type splints or split acrylic splints. The cut end of the arch wire 15 which remains in the patient's mouth is rounded by virtue of the outer bead 17. Accordingly, the cut end of the arch wire 15 does not need any bending or coverage.

The tying plier 20 and the cutting plier 32 are easy to use, they are light in weight, and easy and economical to manufacture. The novel construction of the beaks on the tying plier permits the arch wire 15 to be quickly and easily secured to the arch bar 10 in an efficient manner. The novel construction of the beaks 38 of the cutting plier 32, with its cutting edges 39, recesses 40 and opening 41, permits the free end of the arch wire 15 to be quickly and easily cut off in an efficient manner, and retain the free cut-off end without dropping it into the mouth of the patient.

While it will be apparent that the preferred embodiments of the invention herein disclosed are well calculated to fulfill the objects above stated, it will be appreciated that the invention is susceptible to modification, variation and change.

What is claimed is:

1. An oral surgery treatment assembly for the immobilization of a patient's jaws, comprising in combination:
    (a) a pair of elongated arch bars which each have a plurality of openings therethrough, with each of said openings having a plurality of slits formed around the outer periphery thereof, and each arch bar having a plurality of outwardly extended hooks, and each arch bar being suitable for mounting around the periphery of one jaw of a patient;
    (b) a plurality of arch wires, which each have a retainer member on a first end and a plurality of beads spaced along the length of the wire, for insertion in the mouth of a patient, and for disposal adjacent one or more teeth on each jaw in a patient's mouth, and wherein a second end of each of the arch wires is inserted through one of said plurality of openings through one of the arch bars, and retained in engagement therewith by one of the beads on the arch wire passing through one of said openings, which expand due to said slits to allow passage of a bead, and being seated against the outer face of the arch bar and an adjacent bead being seated against the inner face of the arch bar; and,
    (c) a retainer member is mounted between adjacent opposed pairs of hooks on said jaws for fixing said pair of arch bars together and immobilizing the jaws.

2. The oral surgery treatment assembly for the immobilization of a patient's jaws as defined in claim 1, wherein:
    (a) the retainer member on each of said arch wires is formed so as to embrace a single tooth, so as to secure said one end of each arch wire to a single tooth when the arch wire is tightened relative to the arch bar.

3. The oral surgery treatment assembly for the immobilization of a patient's jaws as defined in claim 2, wherein:
    (a) the retainer member on each of said arch wires is hook shaped.

4. In a method for the immobilization of a patient's jaws, the steps comprising:
    (a) providing a pair of arch bars which each have a plurality of openings therethrough and a plurality of outwardly extended hooks thereon and disposing one arch bar around the outer periphery of each jaw of a patient;
    (b) providing a plurality of arch wires which each have a retainer member on a first end and a plurality of beads spaced along the length of the wire, and disposing each of the arch wires adjacent one or more teeth, on each jaw in a patient's mouth, and inserting a second end of each of the arch wires through one of said plurality of openings through the arch bar on each jaw;
    (c) engaging said second end of each of the arch wires and exerting a tension thereon for tightening each arch wire relative to the arch bar on each jaw, and pulling each arch wire to a tight position with one of the beads thereon disposed against the outer face of the arch bar on each jaw to retain each arch wire in a fixed position, with the arch bar on each jaw clamped against the outer periphery of the teeth on each jaw in a patient's jaw;

(d) cutting the free end portion of said first end of each of the arch wires which extends beyond each of the arch wire beads seated against the outer face of each arch bar on each jaw; and, (e) fixing said jaws together by mounting retainer members between adjacent pairs of hooks on the arch bars on said jaws.

5. The method for the immobilization of a patient's jaw, as defined in claim 4, wherein:

(a) each of said arch wires is disposed between a pair of adjacent teeth, and the retainer member on each arch wire abuts the inner sides of said pair of adjacent teeth.

6. The method for immobilization of a patient's jaws, as defined in claim 4, wherein:

(a) the retainer member on each of said arch wires is formed so as to embrace a single tooth, so as to secure said one end of each arch wire to a single tooth when the arch wire is tightened relative to the arch bar.

7. The method for immobilization of a patient's jaws, as defined in claim 6, wherein:

(a) the retainer member on each of said arch wires is hook shaped.

8. The method for immobilization of a patient's jaws, as defined in claim 4, wherein:

(a) each of the openings on the arch bar is provided with slits around the outer end thereof to permit beads on an arch wire to be passed therethrough in one direction from the inner side of the arch bar to the outer side of the arch bar and retained on the outer side of the arch bar.

9. The method for immobilization of a patient's jaws, as defined in claim 4, wherein:

(a) each of the arch wires is tightened by a typing plier which has one beak that rests against the arch bar and permits an arch wire to pass therethrough, and a second beak for engaging a bead on the arch wire and stretching the arch wire outwardly away from the arch bar.

10. The method for immobilization of a patient's jaws, as defined in claim 9, wherein:

(a) the portion of said one end of each of the arch wires which extends beyond each of the arch wire beads seated against the outer face of the arch wire is cut off by a cutting plier having a pair of cutting beaks which cut the arch wire at the periphery of the arch wire beads seated against the outer face of the arch bar.

* * * * *

UNITED STATES PATENT OFFICE
CERTIFICATE OF CORRECTION

Patent No. 4,202,328   Dated   May 13, 1980

Inventor(s)   Ghassan A. Sukkarie

It is certified that error appears in the above-identified patent and that said Letters Patent are hereby corrected as shown below:

Column 2, line 14, following tying, "pliers" should be --plier--.
Column 2, line 17, following tying, "pliers" should be --plier--.
Column 2, line 21, following cutting, "pliers" should be --plier--.
Column 3, line 50, tying should be inserted before --plier--.

Signed and Sealed this

Fourteenth Day of October 1980

[SEAL]

Attest:

SIDNEY A. DIAMOND

Attesting Officer

Commissioner of Patents and Trademar